Figure 1:
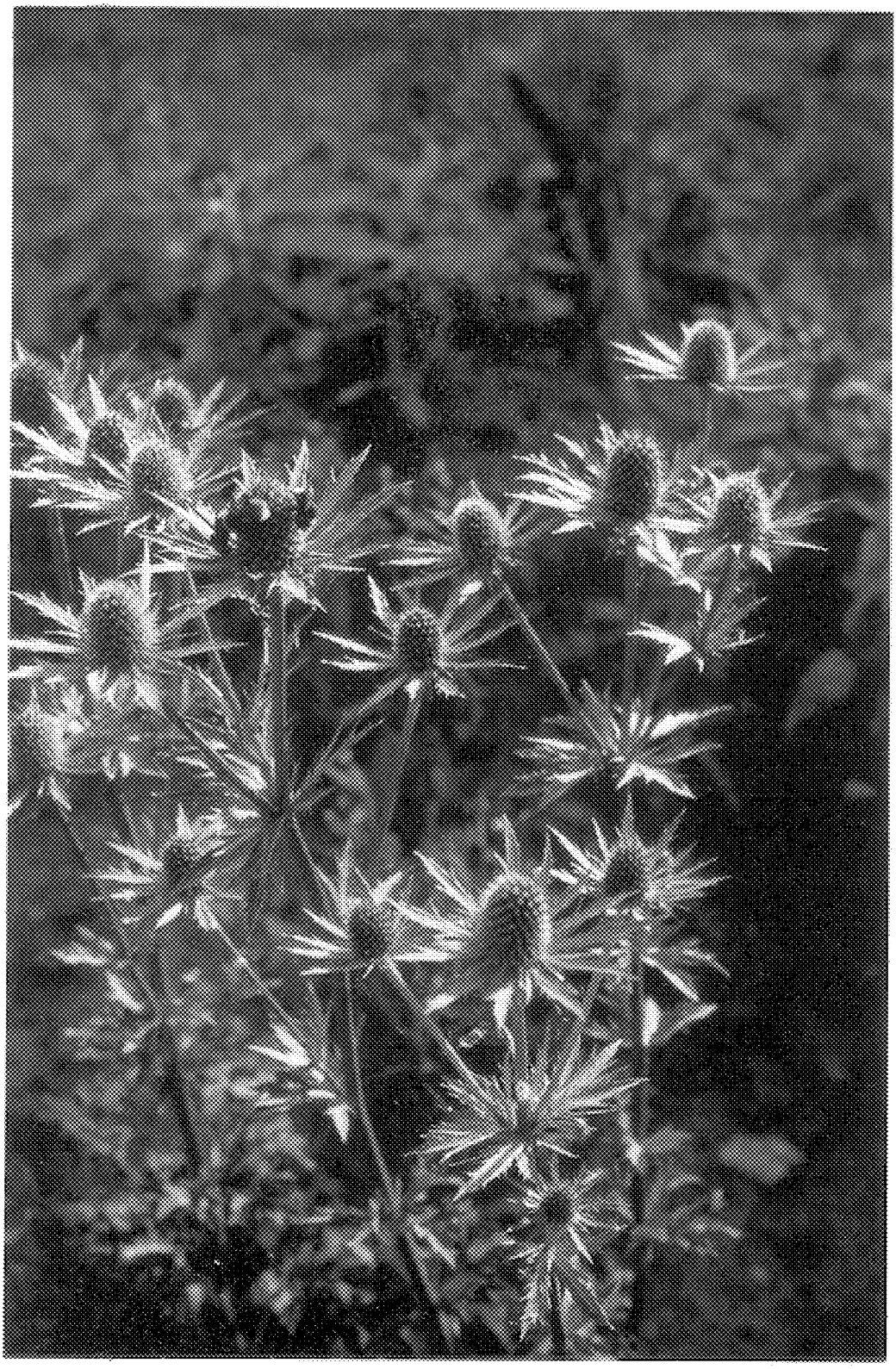

US00PP11088P

United States Patent [19]

Ruigrok

[11] Patent Number: Plant 11,088

[45] Date of Patent: Oct. 12, 1999

[54] ERYNGIUM PLANT NAMED 'SAPPHIRE BLUE'

[75] Inventor: Wouter Ruigrok, Hillegom, Netherlands

[73] Assignee: Blooms of Bressingham, Ltd., Norfolk, United Kingdom

[21] Appl. No.: 08/917,708

[22] Filed: Aug. 26, 1997

[51] Int. Cl.[6] ..... A01H 5/00

[52] U.S. Cl. ..... Plt./263

[58] Field of Search ..... Plt./68.1, 263

*Primary Examiner*—Lynette F. Smith
*Assistant Examiner*—Kent L. Bell
*Attorney, Agent, or Firm*—Foley & Lardner

[57] ABSTRACT

A new and distinct cultivar of plant named 'Sapphire Blue', characterized by the combined features of large, intense lavender blue teasel-like flowers with a collar of spiny bracts, flowering commencing in June and continuing into August, and stems similar in color to the flower.

2 Drawing Sheets

The present invention relates to a new and distinct cultivar of hardy perennial herbaceous plant of the genus Eryngium, known by the cultivar name 'Sapphire blue'. The genus is a member of the Umbelliferae family.

The new cultivar originated as a seedling discovered by the inventor Wouter Ruigrok in Hillegom, The Netherlands and resulted from a cross made by the inventor between an unnamed cultivar of *Eryngium bourgatii* as the seed parent and an unnamed cultivar of *Eryngium alpinum* as the pollen parent.

The first act of asexual reproduction of 'Sapphire Blue' was accomplished when cuttings were taken by the inventor in Hillegom, The Netherlands. This and subsequent asexual reproduction have shown that the unique combination of characteristics as herein disclosed for 'Sapphire Blue' are fixed and retained through successive generations of asexual reproduction.

'Sapphire Blue' has not been observed under all possible environmental conditions. The phenotype may vary with variations in environment such as temperature and light intensity without, however, any variance in the genotype.

The following observations and measurement describe the plants grown in Hillegom, The Netherlands under normal commercial practice. All color values are based on The Royal Horticulture Society (R.H.S.) colour charts.

The following traits have been repeatedly observed and are determined to be basic characteristics of the new cultivar, which in combination distinguish the new cultivar from others:

1. It is a quality flowering perennial with a more intense and truer violet blue, R.H.S. 94 C to R.H.S. 97 C, than any other Eryngium plant known to the inventor. The blue color also extends down the stem, which gives it a unique quality. The absence of viable seed means that the flowers last approximately two weeks longer and will remain intact even after being visited by bees. The leaves are 10 cm in length (compared to 5 cm for the parent *Eryngium bourgatii*) and the flower heads with bracts are up to 7 cm in length (compared to 3–5 cm for the bracts of the parent *Eryngium bourgatii*).

2. The large and intense lavender blue flowers, coupled with the intense lavender blue stems, make an excellent display from June to August.

3. The erect branched stems arising from mainly basal spiny-toothed leaves support the many terminal teasel-like flower heads with their collars of spine toothed bracts.

4. The plant thrives best in full sun and well drained soil although it is tolerant of poorer conditions.

5. The flowers are sterile and bear no viable seed, and bloom for approximately 10–12 weeks, thus being ideal for flower arrangements. The flower stems will remain on the plant intact until damaged by the weather or the onset of winter.

In the photographic drawings, FIG. 1 comprises a closeup view of a typical plant of 'Sapphire Blue', showing in detail the colored stems and the large showy teasel-like flower heads with their collars of spiny bracts.

Figure 2:
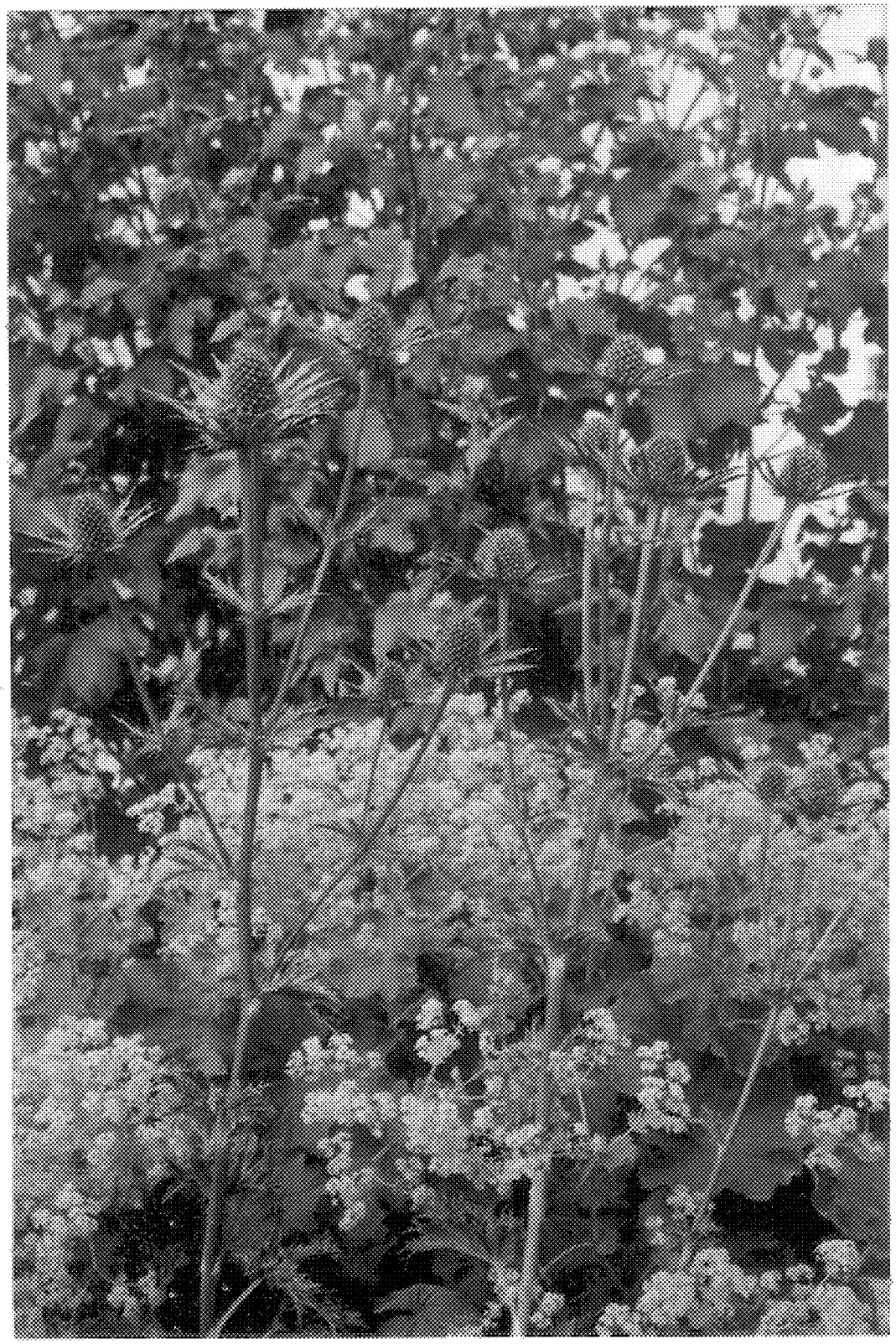

The photograph comprising FIG. 2 illustrates plants of 'Sapphire Blue' (in the foreground) in a border setting.

DETAILED PLANT DESCRIPTION

Parentage: A cross between an unnamed cultivar of *Eryngium bourgatii* (seed parent) and an unnamed cultivar of *Eryngium alpinum* (pollen parent).

Habit: Erect branched stems.

Size: Mature plants are 70 cm in height with a spread of 45 cm.

Number of stems: 5–12 or more.

Root system: Fibrous.

Plant vigor: A perennial that shows vigorous and healthy growth throughout The Netherlands.

Blooming habit: The teasel-like flower heads are borne on erect leafy flower stems that rise from the base of the plant.

Blooming period: From June continuing into early August.

Blooming response: 18–20 weeks from a cutting (observed in a garden situation and also in containers).

Hardiness: Winter hardy throughout The Netherlands. The plant has not been fully tested for maximum summer tolerance above 32° C. (90° F.).

Foliage:

*Arrangement.*—Orbicular, cordate to ovate, spiney-toothed.

*Texture.*—Leathery, sharp spines.

*Length.*—10 cm.

*Width.*—5 cm to 8 cm.

*Petiole length.*—0.5 cm.

*Margins.*—Spinose.

*Apex.*—Aristate.

*Base.*—Cuneate.

*Color.*—Mature leaves upper surface 131 B, under surface 131 C; leaves display silver venation.

Flowers:

*Borne.*—On umbellate erect branched stems typically 9–12 cm in length; stem color is initially green, maturing to between 94 B and 97 B.

*Lastingness of individual blooms.*—Approximately 4–6 weeks.

*Bracts.*—*Normally* 10 in number, each 4–8 in length and approximately 1 cm in width, with spine-like margins and sharp tips; mature bract color on upper surface is between 94 B and 97 B and on lower surface is R.H.S. 94 D.

*Number of flowers per stem.*—Approximately 3–5.

*Flower shape.*—Generally cylindrical, with rounded apex.

*Flower size.*—2.5 to 4 cm, in height and 1.5 to 2.0 cm in width at base.

*Color.*—From a distance, the teasel-like flower head is a mixture of green and lavender blue, with the lavender blue section being approximately 94 C to 97 C in color.

*Carpels.*—2 celled, obscurely ridged.

*Stamens.*—None.

I claim:

1. A new distinct cultivar of Eryngium plant named 'Saphhire Blue', substantially as shown and described.

* * * * *